United States Patent [19]

Boulton et al.

[11] Patent Number: 4,697,012

[45] Date of Patent: Sep. 29, 1987

[54] MORPHOLINO PYRIDYL THIAZOLE COMPOUND

[75] Inventors: David A. Boulton, Edison; Ihor E. Kopka, Newark; Vernon L. Moore, Scotch Plains; Arsenio A. Pessolano, Colonia, all of N.J.

[73] Assignee: Merck & Co., Inc., Rahway, N.J.

[21] Appl. No.: 634,094

[22] Filed: Jul. 25, 1984

[51] Int. Cl.⁴ ............................................ C07D 413/14
[52] U.S. Cl. .................................. 544/124; 546/280; 546/194
[58] Field of Search ........................ 544/124; 514/230

[56] References Cited

U.S. PATENT DOCUMENTS

| 4,080,457 | 3/1978 | Harrison | 514/342 |
| 4,153,703 | 5/1979 | Harrison | 514/365 |
| 4,260,765 | 4/1981 | Harrison | 546/280 |

*Primary Examiner*—Robert W. Ramsuer
*Attorney, Agent, or Firm*—Theresa Y. Cheng; Michael C. Sudol

[57] ABSTRACT

2-Benzyl-4-(4-pyridyl)thiazoles and derivatives thereof have been made from converting a benzyl cyanide to the corresponding thioamide followed by condensation with a 4-bromoacetylpyridine. The thiazole derivatives are found to be effective immunoregulants.

1 Claim, No Drawings

MORPHOLINO PYRIDYL THIAZOLE COMPOUND

BACKGROUND OF THE INVENTION

Immunoregulatory abnormalities have been shown to exist in a wide variety of "autoimmune" and chronic inflammatory diseases, including systemic lupus erythematosis, rheumatoid arthritis, type 1 diabetes mellitus, inflammatory bowel disease and multiple sclerosis. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal tissue system operates.

Similarly, in transplantation, the host lymphocytes recognize the foreign tissue antigens and begin to produce antibodies which lead to the rejection of the transplanted organ.

The end result of an autoimmune or a rejection process is tissue destruction caused by inflammatory cells and the mediators they release. Antiinflammatory agents such as NSAID's and corticosteroids act principally by blocking the effect or secretion of these mediators but do nothing to modify the immunologic basis of the disease. On the other hand, cytotoxic agents such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Accordingly, an object of the present invention is to provide 2-benzyl-4-(4-pyridyl)thiazoles as immunoregulants which will (1) restore the normal balance of the help-and-suppression mechanism of the immune system by acting at an earlier point than the anti-inflammatory agents and (2) induce specific long-term transplantation tolerance through a suppressor cell circuit without increasing the body's susceptibility to infection.

Another object of the present invention is to provide pharmaceutical compositions for administering the active 2-benzyl-4-(4-pyridyl)thiazoles as immunoregulants.

Still a further object of this invention is to provide a method of controlling transplant rejection, autoimmune and chronic inflammatory diseases by administering a sufficient amount of one or more of the active 2-benzyl-4-(4-pyridyl)thiazoles in a mammalian species in need of such treatment.

Finally, it is the object of this invention to provide chemical processes for the preparation of the active 2-benzyl-4-(4-pyridyl)thiazoles.

DETAILED DESCRIPTION OF THE INVENTION

A. Scope of the Invention

This invention relates to immunoregulants of formula:

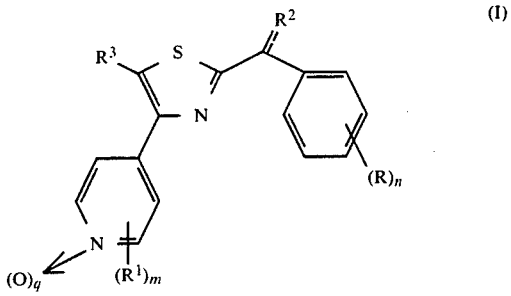

or a pharmaceutical salt thereof
wherein
R and $R^1$ independently are
  (1) hydrogen
  (2) halo especially fluoro, chloro or bromo;
  (3) loweralkoxy especially $C_{1-6}$ alkoxy, e.g., methoxy, ethoxy, isopropoxy, t-butoxy or cyclohexyloxy, or —OCH$_2$O—;
  (4) loweralkylthio especially $C_{1-6}$ alkylthio, or $C_{1-6}$ haloalkylthio e.g., methylthio, ethylthio, trifluoromethylthio or cyclohexylthio;
  (5) loweralkylsulfinyl especially $C_{1-6}$ alkyl sulfinyl, e.g., methyl sulfinyl, i-propyl sulfinyl, and cyclopentyl sulfinyl;
  (6) loweralkylsulfonyl especially $C_{1-6}$ alkylsulfonyl such as methylsulfonyl, ethylsulfonyl and n-butylsulfonyl;
  (7) unsubstituted or substituted phenyl loweralkoxy such as benzyloxy;
  (8) loweralkyl especially $C_{1-6}$ alkyl such as methyl, ethyl, propyl, t-butyl, pentyl, benzyl, cyclopropyl, cyclopentyl or cyclohexyl;
  (9) loweralkenyl especially $C_{2-6}$ alkenyl, for example, vinyl, allyl, and buten-2-yl;
  (10) loweralkanoyl especially $C_{1-6}$ alkanoyl such as formyl, acetyl or i-propanoyl;
  (11) haloloweralkyl especially $C_{1-6}$ haloalkyl such as trifluoromethyl;
  (12) —COOR$_a$ wherein R$_a$ is H or $C_{1-6}$ alkyl;
  (13) aryl especially phenyl or substituted phenyl, e.g., 4-methoxyphenyl, 2,4-difluorophenyl or 3-chlorophenyl; or
  (14) aryloxy especially phenoxy or aryl-S- especially phenyl-S-;
  (15) cyano;
  (16) hydroxyloweralkyl especially hydroxy $C_{1-3}$alkyl such as —CH$_2$OH;
  (17) haloloweralkanoyl especially halo$C_{1-6}$ alkanoyl eq. CF$_3$CO;
  (18) loweralkanoyloxy especially acetyloxy;
  (19) unsubstituted or substituted heteroaryl, for example:
    (a) thienyl;
    (b) benzothienyl;
    (c) furyl;
    (d) benzofuryl;
    (e) pyrryl;
    (f) indolyl;
    (g) thiazolyl;
    (h) benzothiazolyl;
    (i) thiadiazolyl;
    (j) benzothiadiazolyl;
    (k) quinolyl;
    (l) isoquinolyl;

(m) pyridyl;
(n) pyrazinyl;
(o) tetrazolyl; or
(p) triazolyl;
the heteroaryl above can be substituted with one or more functional groups e.g., $C_{1-6}$ alkyl, $C_{1-6}$ alkanoyl, $C_{1-6}$haloalkyl, halo, cyano, or hydroxy $C_{1-3}$ alkyl.
(20) —$NR_aCOR_b$ wherein $R_a$ and $R_b$ independently are H or $C_{1-6}$ alkyl;
(21) —$NO_2$;
(22) —$NR_aR_b$;
(23) —$OR_a$;
(24) —$CONR_aR_b$
(25) —$COR_a$;
(26) —$NR_aCONR_bR_b$;
(27) —$NR_aCOR_b$;
(28) —$OCOR_a$;
(29) —$SCOR_a$; or
(30) —$OCH_2O$—;

$R^2$ can be connected to the benzyl carbon with a single or a double bond: for double bond-connection, $R^2$ can only be =O, =S, =$NR_a$, or =CH—$R_c$ wherein $R_c$ is $R_a$, $OR_a$, or halo; for single-bond connection, there can be one or two sets of $R^2$ and each $R^2$ independently is $R_c$;

$R^3$ is $R_a$, halo or haloloweralkyl;
n is 1 to 4;
m is 1 to 5; and
q is 0 or 1.

In a preferred embodiment of this invention R and $R^1$ independently are
(1) hydrogen;
(2) halo;
(3) —$OR_a$;
(4) $C_{1-6}$ alkylthio;
(5) $C_{1-6}$ alkyl;
(6) —$CF_3$;
(7) phenyl;
(8) —CN;
(9) —$NR_aCOR_b$;
(10) —$NO_2$;
(11) —$NR_aR_b$;
(12) —$CONR_aR_b$
(13) —$NR_aCONR_bR_a$; or
(14) heteroaryl or substituted heteroaryl especially pyridyl thienyl, or thiazolyl;

$R^2$ is hydrogen;
$R^3$ is $R_a$;
n is 1 or 2;
m is 1 or 2; and
q is 0 or 1.

In a more preferred embodiment of this invention, R and $R^1$ independently are
(1) hydrogen;
(2) $C_{1-6}$ alkyl;
(3) —$NR_aR_b$;

$R^2$ is hydrogen or F;
$R^3$ is H;
n is 1 or 2;
m is 1 or 2; and
q is 0.

B. Preparation of the compounds within the scope of the present invention

The compounds of formula (I) are prepared from known starting materials according to the following synthetic schemes:

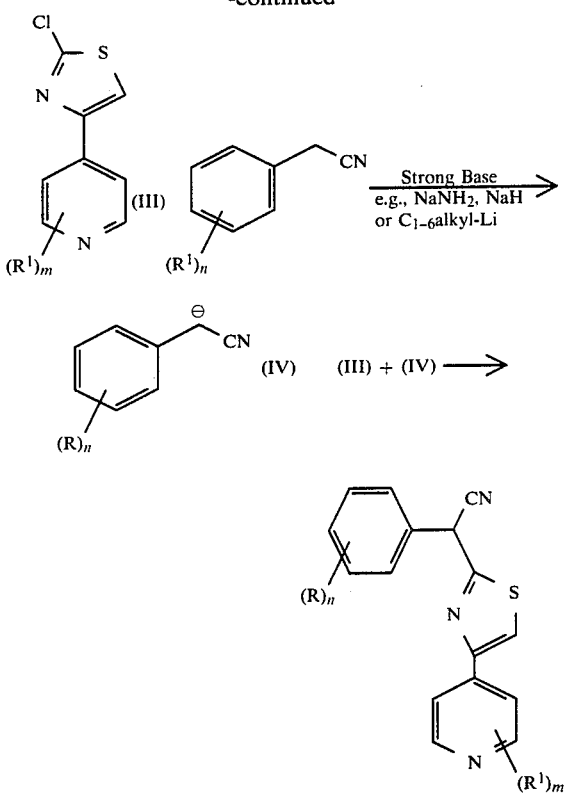

C. Utility of the compounds within the scope of the invention

This invention also relates to a method of treatment of patients suffering from autoimmune diseases. More specifically, it relates to a method of treatment involving the administration of a compound of formula (I) as the active constituent.

For the treatment of autoimmune diseases a compound of formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1) inert diluents such as calcium carbonate, sodium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be (1) suspending agents such as sodium carboxymethylcellulose, methylcellulose, hydroxypropylmethylcellulose, sodium alginate, polyvinylpyrrolidone, gum tragacanth and gum acacia;

(2) dispersing or wetting agents which may be
 (a) a naturally-occurring phosphatide such as lecithin,
 (b) a condensation product of an alkylene oxide with a fatty acid, for example, polyoxyethylene stearate,
 (c) a condensation product of ethylene oxide with a long chain aliphatic alcohol, for example, heptadecaethyleneoxycetanol,
 (d) a condensation product of ethylene oxide with a partial ester derived from a fatty acid and a hexitol such as polyoxyethylene sorbitol monooleate, or
 (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

A compound of (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the immunoregulants are employed.

Dosage levels of the order from about 0.5 mg to about 100 mg per kilogram of body weight per day are useful in the treatment of the above-indicated conditions (from about 25 mg to about 5 gms. per patient per day).

The amount of active ingredient that may be combined with the carrier materials to produce a single dosage form will very depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

D. Biological evidence in support of utility of the compounds within the scope of the invention It has been found that the compounds of formula (I) have immunoregulatory activities and are thereby useful in the treatment of various "autoimmune" and chronic inflammatory diseases. They may also be useful in the prevention of rejection of "donor" organs in transplantation operations. The following tables illustrate and support the utility of the compounds of the present invention:

TABLE I

The Delayed Hypersensitivity Assay

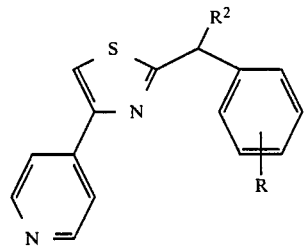

| | Dosage (mg/kg) | Inhibition % |
|---|---|---|
| (a) $R^2$ = H: | | |
| R | | |
| H | 0.01 | 21.8 |
| | 0.1 | 70.2 |
| | 30 | 75.2 |
| o-$NH_2$ | 0.01 | 82.2 |
| | 0.1 | 93.6 |
| | 10.0 | 52.8 |
| o-$NHCOCH_3$ | 0.1 | 32.6 |
| | 10.0 | 52.8 |
| | 100.0 | 75.5 |
| o-$NHCONH_2$ | 0.01 | 40.4 |
| | 10.0 | 31.4 |
| o-OH | 0.01 | 15.1 |
| | 0.1 | 16.4 |
| m-$CH_3$ | 0.1 | 49.1 |
| | 10.0 | 64.8 |
| | 100.0 | 71.2 |
| p—F | 0.1 | 11.7 |
| | 1.0 | 60.8 |
| | 10.0 | 40.9 |
| p-$NO_2$ | 0.01 | 32.4 |
| | 0.1 | 40.6 |
| | 10.0 | 65.2 |
| | 100.0 | 82.2 |
| p-$C_6H_5$ | 10.0 | 36.4 |
| (b) R = H: | | |
| $R^2$ | | |
| OH | 0.1 | 32 |
| | 1.0 | 31 |
| | 10.0 | 55 |
| $CH_2OH$ | 0.1 | 51 |
| | 1.0 | 65 |
| | 10.0 | 27 |
| CN | 0.1 | 58 |
| | 1.0 | 46 |
| CHO | 10.0 | 63 |
| F,F | 1.0 | 49 |
| | 10.0 | 63 |

TABLE II

The Delayed Hypersensitivity Assay

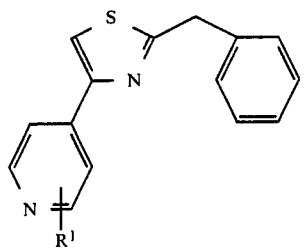

| R¹ | Dosage (mg/ml) | Inhibition % |
|---|---|---|
| 2-Cl | 0.01 | 52.6 |
| | 0.1 | 64.7 |
| | 10.0 | 77.6 |
| | 100.0 | 80.1 |
| N—oxide | 0.01 | 46.0 |
| | 0.1 | 55.6 |
| | 10.0 | 71.8 |
| | 100.0 | 93.4 |
| 2-morpholino | 0.01 | 26.1 |
| | 0.1 | 33.8 |
| | 10.0 | 44.3 |
| | 100.0 | 45.1 |
| 2-CN | 10 | 36.6 |

Animals (female BALB/C mice) are sensitized with $5 \times 10^5$ SRBC(sheep red blood cells)/0.5 ml by intravenous (tail vein) injection. One hour prior to challenge, animals are dosed with the drugs in question, p.o. On day four the animals are challenged with $5 \times 10^8$ SRBC/0.05 ml in the hind foot pad. Footpad volume is measured by a mercury displacement apparatus before challenge and 24 hrs post challenge. Percent inhibition of footpad swelling is calculated by comparing the increase in footpad volume of test group to the control group.

EXAMPLE 1

α-Bromo-4-acetylpyridine hydrobromide

A twelve-liter three neck flask fitted with an efficient mechanical stirrer, 250 mL dropping funnel, and internal thermometer was charged with glacial acetic acid (5000 mL), pyridinium bromide perbromide (90%, 830 g, 2.60 mol) and 30% hydrobromic acid in acetic acid (525 mL). After stirring at room temperature for ninety minutes, 4-acetylpyridine (250 g, 2.07 mol) was added dropwise over forty-five minutes. Upon completion of the addition the reaction mixture was cooled with an ice bath to 15° C. and the product, which had precipitated, was collected by filtration, washed with ether and air dried. The crude α-bromo-4-acetylpyridine hydrobromide (566.3 g, 97%) was sufficiently pure for subsequent reactions. mp. 177.5°–182.0° C.

EXAMPLE 2

Benzylthioamide

A mixture of benzylcyanide (20.0 g, 0.17 mol) and sodium hydrosulfide nonahydrate (2.50 g) and absolute ethanol (100 mL) in a Wheaton pressure bottle was cooled to −15° C. A stream of hydrogen sulfide was bubbled into this mixture for twenty minutes and the bottle sealed and warmed on a steam bath for 2.5 days. The mixture was cooled to −25° C., the seal broken, and the mixture flushed with a stream of nitrogen for one hour. The resulting mixture was diluted with water (300 mL), extracted with ether (3×100 mL), and the combined organic extracts washed with brine (100 mL), dried (MgSO₄), and concentrated to a yellow oil which crystallized from hexane/ethyl acetate. The purified benzylthioamide was obtained as white needles (23.5 g, 91%). mp. 97°–98° C.

EXAMPLE 3

2-Benzyl-4-(4-pyridyl)thiazole

A mixture of α-bromo-4-acetylpyridine hydrobromide (63.0 g, 0.22 mol) and benzylthioamide (34.0 g, 0.22 mol) in absolute ethanol (600 mL) was warmed on a steam bath for ninety minutes. Upon cooling in an ice-bath, the hydrobromide which had precipitated was collected by filtration and washed with ether. The hydrobromide salt was suspended in water (600 mL), basified with 2.5N sodium hydroxide and extracted with ether (3×300 mL). The combined organic extracts were washed with brine (2×400 mL), dried (MgSO₄), and concentrated. Recrystallization of the resulting yellow oil from hexane/ethyl acetate afforded 2-benzyl-4-(4-pyridyl)thiazole (33.0 g, 59%) as white crystals. mp. 88°–89° C.

In a manner essentially the same as that used in Example 1, the following compounds were prepared from α-bromo-4-acetylpyridine hydrobromide and an appropriate starting material:

| Product | Starting Material | Yield % of Product | m.p. (°C.) |
|---|---|---|---|
| (1) 2-(p-fluoro-benzyl)-4-(4-pyridyl)thiazole | p-fluorobenzyl-thioamide | 25% | 66–68 |
| (2) 2-(m-methyl-benzyl)-4-(4-pyridyl)thiazole dihydrochloride | m-methylbenzyl-thioamide | 54% | 152–154 |

EXAMPLE 4

2-(o-Aminobenzyl)-4-(4-pyridyl)thiazole

A solution of 2-(o-acetamidobenzyl)-4-(4-pyridyl)thiazole (2.30 g, 0.007 mol) in concentrated hydrochloric acid (2 mL) and ethanol (3 mL) was refluxed for 3 hours, allowed to cool, diluted with water (2 mL) and methylene chloride (5 mL), and basified with 2.5N sodium hydroxide. The layers were separated and the aqueous layer reextracted with chloroform (2×). The combined organic extracts were dried over potassium carbonate, concentrated, and chromatographed through a short column of silica gel to afford 2-(o-aminobenzyl)-4-(4-pyridyl)thiazole (1.30 g, 65%). mp. 179°–181° C. dec.

EXAMPLE 5

2-(p-Nitrobenzyl)-4-(4-pyridyl)thiazole

A solution of 2-benzyl-4-(4-pyridyl)thiazole (4.50 g, 0.018 mol) in chloroform (25 mL) was added dropwise to concentrated sulfuric acid (15 mL). The resulting mixture was cooled to 10° C. and fuming nitric acid (1.45 g, 0.97 mL) carefully added dropwise such that the reaction temperature did not exceed 40° C. The mixture was allowed to stir for thirty minutes, carefully neutralized with saturated sodium carbonate and the layers separated. The aqueous layer was reextracted with chloroform (2×25 mL) and the combined organic extracts were washed with brine (20 mL), dried over magnesium sulfate, and concentrated to afford a crude product (4.6 g). Several recrystallizations from hexane/ethyl acetate afforded pure 2-(p-nitrobenzyl)-4-(4-pyridyl)thiazole. mp. 140°-142° C.

EXAMPLE 6

2-Phenyl-2-[4-(4-pyridyl)-2-thiazolyl)]acetaldehyde

To a solution of 2-benzyl-4-(4-pyridyl)thiazole (4.00 g, 0.016 mol) and tetramethylethylenediamine (2.5 mL) in dry tetrahydrofuran (35 mL) at −78° C. under nitrogen atmosphere was added dropwise n-butyl lithium (1.6M in hexane, 11.4 mL). The resulting dark mixture was allowed to stir at −78° C. for 15 minutes, warmed to 0° C. for 2 hours, then cooled to −78° C. Ethyl formate (1.47 mL) was added dropwise and the mixture allowed to stir at −78° C. for 30 minutes then at 0° C. for one hour. The reaction mixture was quenched with methanol, concentrated, and chromatographed over silica gel. Recrystallization from hexane/ethyl acetate afforded 2-phenyl-2-[4-(4-pyridyl)-2-thiazolyl]acetaldehyde (1.76 g, 39%). mp. 163°-164° C.

EXAMPLE 7

2-Phenyl-2-[4-(4-pyridyl)-2-thiazolyl] ethanol

To a solution of 2-phenyl-2-[4-pyridyl)-2-thiazolyl]acetaldehyde (0.50 g, 0.0018 mol) in absolute ethanol (5 mL) at 0° C. was added sodium borohydride (71 mg) and the mixture allowed to warm to room temperature and stir for 4 hours. The reaction was quenched with dilute hydrochloric acid and the ethanol removed in vacuo. The resulting mixture was diluted with water, neutralized with aqueous sodium bicarbonate, and extracted with methylene chloride. The organic extract was dried over sodium sulfate, concentrated, and chromatographed over silica gel (1:4 methylene chloride/ethyl acetate as eluant) to afford 2-phenyl-[4-(4-pyridyl)-2-thiazolyl]-ethanol (360 mg, 72%). mp. 120°-122° C.

EXAMPLE 8

1,1-Difluoro-1-phenyl-1-[4-(4-pyridyl)-2-thiazolyl]-methane

Step A: Preparation of 2,2-difluoro-2-phenylacetamide

A solution of methyl 2,2-difluoro-2-phenylacetate (14.28 g, 0.077 mol) in absolute ethanol (100 mL) was saturated with anhydrous ammonia. The resulting mixture was allowed to stir at room temperature overnight then concentrated to dryness. The resulting crude product was recrystallized from hexane/ethyl acetate to afford 2,2-difluoro-phenylacetamide (12.2 g, quantitative). mp. 113°-114° C.

Step B: Preparation of 2,2-difluoro-2-phenylthioacetamide

To a solution of 2,2-difluoro-2-phenylacetamide (2.0 g, 0.0128 mol) in dry dioxane (15 mL) was added phosphorous pentasulfide (3.40 g) and sodium bicarbonate (4.30 g). The heterogeneous mixture was sonicated at 50° C. for 2.5 hours and, after cooling, the insoluble material was removed by filtration. The filter cake was washed with ether (2×50 mL) and the combined filtrates washed with dilute hydrochloric acid. The organic layer was dried over sodium sulfate, concentrated, and chromatographed through a short column of silica gel to afford 2,2-difluoro-2-phenylthioacetamide (1.65 g, 75%). mp. 99°-100° C.

Step C: Preparation of 1,1-difluoro-1-phenyl-[4-(4-pyridyl)-2-thiazolyl]methane

To a solution of 2,2-difluoro-2-phenylthioacetamide (1.57 g, 0.0092 mol) in 95% ethanol (20 mL) was added α-bromo-4-acetylpyridine hydrobromide (3.20 g, 0.012 mol) and the mixture warmed on a steam bath for thirty minutes. The product was isolated in the usual way and recrystallized from ethyl acetate/hexane to afford 1,1-difluoro-1-phenyl-[4-(4-pyridyl)-2-thiazolyl]methane (1.27 g, 48%). mp. 54.5°-55.5° C.

EXAMPLE 9

2-Phenyl-2-[4-(4-pyridyl)-2-thiazolyl]acetonitrile

Step A: Preparation of 2-hydroxy-4-(4-pyridyl)thiazole

A mixture of α-bromo-4-acetylpyridine hydrobromide (140.0 g, 0.50 mol) and potassium thiocyanate (53.4 g, 0.55 mol) in absolute ethanol (1500 mL) was heated to reflux for two hours. To the resulting mixture was added concentrated hydrochloric acid (250 mL) and water (500 mL) and reflux continued for five hours. After cooling, the crystallized solid was collected by filtration and washed with ethanol. The resulting material was suspended in water and neutralized with aqueous sodium bicarbonate to obtain, after filtration and drying, 2-hydroxy-4-(4-pyridyl)thiazole 39.0 g, 44%). mp. 250° C.

Step B: Preparation of 2-chloro-4-(4-pyridyl)thiazole

A mixture of 2-hydroxy-4-(4-pyridyl)thiazole (17.8 g, 0.10 mol) in phosphorous oxychloride (175 mL) was heated at 140° C. for 48 hours then quenched by carefully pouring onto ice (4000 mL). The resulting mixture was basified with 50% sodium hydroxide to pH 9 and extracted with methylene chloride (5×400 mL). The combined extracts were dried over sodium sulfate, concentrated, and chromatographed over silica gel (ethyl acetate as eluant). Recrystallization from ethyl acetate/hexane afforded 2-chloro-4-(4-pyridyl)thiazole (5.70 g, 29%). mp. 124°-125° C.

Step C: Preparation of 2-Phenyl-2-[4-(4-pyridyl)-2-thiazolyl]acetonitrile

To a solution of 2-chloro-4-(4-pyridyl)thiazole (1.00 g, 0.005 mol) and benzylcyanide (1.18 g, 0.010 mol) in dry toluene (10 mL) at 5° C. was added sodamide (400 mg, 0.010 mol) and the mixture heated to 100° C. for 20 minutes. After cooling, the mixture was quenched with water, the layers separated, and the aqueous phase washed with methylene chloride (2×50 mL). The combined extracts were dried over sodium sulfate, concentrated, and chromatographed through silica gel (3:1 ethyl acetate/methylene chloride as eluant). After decolorizing with charcoal, recrystallization from hexane/ethyl acetate afforded 2-phenyl-2-[4-(4-pyridyl)-2-thiazolyl]acetonitrile (115 mg, 8%). mp. 110°-111° C.

EXAMPLE 10

2-(o-Bromobenzyl)-4-(4-pyridyl)thiazole

To a stirred suspension containing o-bromobenzylthioamide (3.00 g, 0.013 mol) and α-bromo-4-acetylpyridine hydrobromide (3.90 g, 0.014 mol) in dry acetone (75 mL) was added potassium carbonate (9.70 g, 0.070 mol) and the resulting mixture refluxed for 24 hours. After cooling the reaction mixture was filtered and the filtrate concentrated. The resulting brown oil was taken up in ethyl acetate (75 mL), washed with water (50 mL), dried over sodium sulfate, and filtered through a short pad of silica gel. After concentration the crude product was triturated from hexane to afford 2-(o- bromobenzyl)-4-(4-pyridyl)thiazole (3.00 g, 70%). mp. 114°-116° C.

EXAMPLE 11

2-(o-cyanobenzyl)-4-(4-pyridyl)thiazole hydrochloride

A mixture of 2-(o-bromobenzyl)-4-(4-pyridyl)thiazole (2.30 g, 0.007 mol) and copper cyanide (2.30 g, 0.026 mol) in dry N-methylpyrrolidinone (25 mL) was heated under nitrogen at 175° C. for six hours. After cooling the reaction mixture was filtered and the filtrate triturated with 1:1 water/concentrated ammonium hydroxide (4×50 mL). The resulting dark brown solid was warmed in dioxane (200 mL), filtered through silica gel, and concentrated in vacuo to an oily residue. The residue was taken up in ether (75 mL), filtered through celite, and the filtrate acidified with dry hydrochloric acid. The product which crystallized was collected and recrystallized (2×) from ethanol/ether to afford 2-(o-cyanobenzyl)-4-(4-pyridyl)thiazole hydrochloride (800 mg, 29%). mp. 240° C. dec.

EXAMPLE 12

2-(o-carboxamidobenzyl)-4-(4-pyridyl) thiazole

Solid 2-(o-cyanobenzyl)-4-(4-pyridyl)thiazole (2.00 g, 0.007 mol) was added carefully in portions to concentrated sulfuric acid (35 mL) at 0° C. After stirring at room temperature overnight the reaction was worked up by pouring into ice water (50 mL) and carefully neutralizing the aqueous mixture with sodium bicarbonate. The mixture was extracted with ethyl acetate, dried over potassium carbonate, and concentrated. Recrystallization from ethyl acetate/hexane afforded 2-(o-carboxamidobenzyl)-4-(4-pyridyl)thiazole (1.12 g, 54%). mp. 165°-166° C.

EXAMPLE 13

1-Phenyl-1-[4-(4-pyridyl)-2-thiazolyl]methanone

To a mixture of 2-benzyl-4-(4-pyridyl)thiazole (3.00 g, 0.01 mol) and potassium permanganate (3.16 g, 0.02 mol) in benzene (30 mL) and water (60 mL) was added tetrahexyl ammonium iodide (0.96 g, 0.02 mol). The biphasic mixture was heated at reflux for 15 hours. After cooling the organic layer was separated and concentrated. The residue was taken up in ethyl acetate, filtered through silica gel, concentrated and chromatographed (ethyl acetate/hexane as eluant). Recrystallization from ethyl acetate/hexane afforded 1-phenyl-1-[4-(4-pyridyl)-2-thiazolyl]methanone (0.50 g, 11%). mp. 135°-136° C.

EXAMPLE 14

1-Phenyl-1-[4-(4-pyridyl)-2-thiazolyl]methanol

To a solution of 1-phenyl-1-[4-(4-pyridyl)-2-thiazolyl]methanone (675 mg, 0.0025 mol) in methanol (40 mL) was added sodium borohydride (300 mg, 0.0079 mol) in portions and the mixture allowed to stir at room temperature for one hour. The reaction mixture was concentrated, diluted with water, and extracted with ether (3×25 mL). The combined extracts were washed with brine, dried over magnesium sulfate, concentrated, and chromatographed. Recrystallization from hexane/ethyl acetate afforded 1-phenyl-1-[4-(4-pyridyl)-2-thiazolyl)methanol (300 mg, 45%). mp. 146°-147° C.

EXAMPLE 15

4-[2-(Phenylmethyl)-4-thiazolyl]pyridine-1-oxide

To a suspension of n-chloroperbenzoic acid (14.5 g) in dry methylene chloride (150 mL) was added a solution of 2-benzyl-4-(4-pyridyl)thiazole (15.1 g, 0.06 mol) in methylene chloride (125 mL) over thirty minutes. The mixture was allowed to stir overnight at room temperature then an additional portion of m-chloroperbenzoic acid (3.00 g) was added. After an additional six hours of stirring the mixture was extracted with saturated sodium bicarbonate (3×100 mL). The organic layer was dried over sodium sulfate, and concentrated to a total volume of 75 mL. Dilution with ether (200 mL) afforded 4-[2-(phenylmethyl)-4-thiazolyl]pyridine-1-oxide (15.3 g, 95%). Recrystallization from ethanol/ether afforded an analytical sample. mp. 170°-172° C.

EXAMPLE 16

2-Benzyl-4-(2-chloro-4-pyridyl)thiazole

A suspension of 4-[2-(phenylmethyl)-4-thiazolyl]pyridine-1-oxide (1.00 g, 0.0037 mol) in phosphorous oxychloride (10.0 g) was warmed on a steam bath overnight. After cooling the reaction mixture was concentrated and the residue treated with an excess of aqueous sodium bicarbonate. The tan precipitate was collected, taken up in methylene chloride (15 mL) and ether (75 mL), and filtered through celite. The filtrate was concentrated to a total volume of 10 mL and diluted with hexane (50 mL). The product which crystallized on standing was collected and dried to afford 2-benzyl-4-(2-chloro-4-pyridyl)thiazole (325 mg, 31%). mp. 104°-106° C.

EXAMPLE 17

2-Benzyl-4-[2-(1-piperidyl)-4-pyridyl]thiazole

A solution of 2-benzyl-4-(2-chloro-4-pyridyl)thiazole (1.00 g, 0.0035 mol) in piperidine (15 mL) was heated to reflux for 16 hours. The reaction mixture was concentrated, taken up in ether (50 mL), filtered through celite, and the filtrate washed with water (2×). The ether layer was dried and concentrated. The residue was taken up in ethanol (20 mL) and treated with an excess of dry hydrochloric acid. Careful dilution with ether afforded 2-benzyl-4-[2-(1-piperidyl)-4-pyridyl)thiazole]-dihydrochloride (525 mg, 49%). mp. 145° C.

EXAMPLE 18

2-Benzyl-4-(3-methoxy-4-pyridyl)thiazole

Step A: Preparation of 3-methoxy-4-acetylpyridine

A dry 50 mL three neck flask fitted with a reflux condenser and internal thermometer was charged with dry methanol (20 mL). Sodium (516 mg, 0.022 mol) was added in portions and after all the sodium had dissolved the methanol was removed by distillation. The resulting sodium methoxide was cooled and a mixture of methyl-3-methoxyisonicotinoate (2.50 g, 0.015 mol) and methyl acetate (6.65 g, 0.090 mol) was added dropwise. The mixture was refluxed for four hours, allowed to cool and dissolved in water (9.0 mL) and concentrated hydrochloric acid (6.0 mL). The resulting mixture was heated to reflux for 2.5 hours, cooled, and basified with 5% sodium bicarbonate. The mixture was extracted with chloroform (4×50 mL) and the combined extracts dried over sodium sulfate, concentrated, and chromatographed through a short column of silica gel to afford 3-methoxy-4-acetylpyridine (1.05 g, 46%). mp. 36°–37° C.

Step B: Preparation of α-bromo-3-methoxy-4-acetylpyridine hydrobromide

A solution of pyridinium hydrobromide perbromide (2.33 g, 0.0073 mol) in acetic acid (20 mL) containing 31% hydrobromic acid in acetic acid (1.85 mL) was stirred at room temperature for four hours. The mixture was cooled to 17° C. and a solution of 3-methoxy-4-acetylpyridine (1.02 g, 0.0062 mol) in acetic acid (5 mL) was added. The cooling bath was removed and after about thirty minutes a yellow solid was deposited. Ether (25 mL) was added and the crude α-bromo-3-methoxy-4-acetylpyridine hydrobromide (1.60 g) was collected by filtration washed with ether and air dried.

Step C: Preparation of 2-benzyl-4-(3-methoxy-4-pyridyl)thiazole

A mixture of α-bromo-3-methoxy-4-acetylpyridine hydrobromide (1.56 g) and benzyl thioamide (758 mg, 0.005 mol) in absolute ethanol (45 mL) was heated to reflux for thirty minutes. Upon cooling a yellow solid precipitated. Ether (25 mL) was added and the precipitate collected and washed with ether. The filtrate was concentrated and along with the filter cake was dissolved in water (20 mL). The mixture was basified with 5% sodium bicarbonate and extracted with methylene chloride (3×25 mL). The combined extracts were dried over sodium sulfate, concentrated, and chromatographed over silica gel (1:1 ethyl acetate/hexane as eluant. Recrystallization from hexane/methylene chloride afforded 2-benzyl-4-(3-methoxy-4-pyridyl)thiazole (734 mg, 42%). mp. 76°–77° C.

What is claimed is:

1. The compound 2-benzyl-4-[2-(morpholino)-4-pyridyl]thiazole.

* * * * *